United States Patent [19]

Schmitt et al.

[11] 4,372,836
[45] Feb. 8, 1983

[54] LIGHT CURABLE ACRYLIC DENTAL COMPOSITION WITH CALCIUM FLUORIDE PIGMENT

[75] Inventors: Werner Schmitt; Robert Purrmann, both of Starnberg; Peter Jochum, Pilsensee; Heinz-Joachim Hübner, Seefeld, all of Fed. Rep. of Germany

[73] Assignee: Espe Fabrik Parmazeutischer Praparate GmbH, Fed. Rep. of Germany

[21] Appl. No.: 185,903

[22] PCT Filed: Jan. 2, 1979

[86] PCT No.: PCT/DE79/00001
§ 371 Date: Jul. 31, 1979
§ 102(e) Date: Jul. 31, 1979

[30] Foreign Application Priority Data

Jan. 3, 1978 [CH] Switzerland ............................ 38/78

[51] Int. Cl.³ .......................... C08F 2/50; C08K 3/16
[52] U.S. Cl. .............................. 204/159.23; 523/116; 524/779; 524/783; 433/228
[58] Field of Search .................... 204/159.23, 159.24; 260/42.52; 433/228; 523/116, 514; 524/436, 779

[56] References Cited

U.S. PATENT DOCUMENTS

| | | | |
|---|---|---|---|
| 3,427,366 | 2/1969 | Verdol et al. ...................... | 525/126 |
| 3,709,866 | 1/1973 | Waller .............................. | 260/27 R |
| 3,804,794 | 4/1974 | Schmitt et al. ..................... | 433/228 |
| 3,969,499 | 7/1976 | Lee et al. .......................... | 433/228 |
| 4,046,578 | 9/1977 | Smith .............................. | 106/35 |
| 4,131,729 | 12/1978 | Schmitt et al. .................... | 204/159.23 |
| 4,192,795 | 3/1980 | Madhaven et al. ............... | 260/42.52 |
| 4,267,097 | 5/1981 | Michl et al. ...................... | 260/42.52 |

FOREIGN PATENT DOCUMENTS

| | | |
|---|---|---|
| 2831 | 9/1980 | European Pat. Off. . |
| 2126419 | 12/1971 | Fed. Rep. of Germany . |
| 2135645 | 3/1973 | Fed. Rep. of Germany . |
| 2646416 | 5/1977 | Fed. Rep. of Germany . |
| 765693 | 3/1934 | France . |
| 168872 | 4/1934 | Switzerland . |
| 569974 | 6/1945 | United Kingdom . |

OTHER PUBLICATIONS

Solomatov et al.; Chem. Abstracts 076-06-025926P; (1976).
Chernyavskaya et al.; Chem. Abstracts 078-20-1255-54A; (1978).
Practical Spectroscopy, Harrison et al., Prentice Hall 1948 pp. 52 & 53.
Kirk-Othmer "Encyclopedia..." 2nd Ed. vol. 9, 1966, pp. 574, 581 & 582, (Gall).

Primary Examiner—Paul Lieberman
Assistant Examiner—A. H. Koeckert
Attorney, Agent, or Firm—Burns, Doane, Swecker & Mathis

[57] ABSTRACT

An improved opaque, photopolymerizable dental filling material is provided comprised of acrylic acid ester compounds containing mono and/or polyfunctional acrylic or methacrylic ester compounds, photoinitiators, pigments and possibly activators and silicon dioxide or silicate fillers, the improvement comprising the presence of finely divided calcium fluoride as a white pigment in a quantity of from 1–20 percent by weight. The presence of the calcium fluoride enables an opaque effect to be achieved without reducing the permeability of the filling material to polymerization radiation.

7 Claims, No Drawings

LIGHT CURABLE ACRYLIC DENTAL COMPOSITION WITH CALCIUM FLUORIDE PIGMENT

DESCRIPTION

Tooth filler material on the basis of unsaturated polyesters, e.g., diacrylate or dimethacrylate ester compounds which can be hardened quickly in situ by light in the presence of certain polymerization initiators, have been known for a long time. Thus, in British Pat. No. 569,974, photopolymerizable dental masses for fillings of teeth have been described, which consist of a mixture of polyacrylates and acrylate ester monomers and contain benzoin as photoinitiator. These masses are then hardened by irradiation by means of a UV light source, after application in the mouth. Also German OS 21 26 419 or the corresponding U.S. Pat. No. 3,709,866 as well as the German OS 21 35 645 describe such dental masses polymerizable by UV light, which additionally contain polymerization catalysts in order to achieve a quick and complete hardening. The light sensitivity of the polymerizable masses on the basis of acrylic acid esters can be further increased by certain activators, especially aliphatic or aromatic or mixed aliphatic-aromatic phosphites, as described in the German OS 26 46 416.

In order to achieve a safe and especially a complete polymerization and hardening of the fillings of the teeth, it is necessary for the material that is to be hardened in situ by radiation to have a good permeability for short wave light so that the rays can penetrate not only the surface area but also deep into the mass down to its rear surface, in order to initiate there as well the polymerization at the same intensity as is the case on the surface of the fillings facing the radiation source.

This good light permeability of the tooth filler masses, however, has some cosmetic disadvantages when they are used in the frontal area of the teeth for approximal cavities that no longer possess the palatinal wall, since in such a case these translucent fillers have a dark appearance because of the dark background of the oral cavity. A similar problem results in case of fillings of a small thickness lacking a tooth-colored background, e.g., with a translucently visible, protective base. Obviously, a difficult problem results in such a case of light hardenable tooth filler masses. That is, if for cosmetic reasons one uses a white pigmented material, e.g., a mass filled with lithopone, titanium dioxide or zinc oxide for fillings in such locations, only a thin surface layer of the tooth filler is hardened upon irradiation with light, because these pigments absorb not only the visible, but also more or less strongly the radiation in the UVA and the near-UVA range of the spectrum (about 320–500 nm). Consequently, such a filling must be built up by layers and hardening by irradiation must be carried out after the application of each thin layer. As a result, however, the dentist is under a heavy strain and the treatment is so greatly delayed that the advantages of the photohardenable tooth filler material are lost in the case of such applications in the frontal area of the teeth. Therefore, they have heretofore not established themselves for such lateral tooth fillings in the frontal area of the set of teeth.

Now, it was surprisingly discovered that a sufficiently penetrating hardening can be achieved if finely divided calcium fluoride is used as a pigmenting filler for these photohardenable dental masses. According to this invention, this pigment is preferably used in the case of such tooth filler material for the frontal area in a quantity of 1–20% by weight, most preferably 2–15% by weight, relative to the filler mixture. Calcium fluoride is physiologically harmless. The particle size is preferably below 60μ; calcium fluoride of <10μ being especially suitable. If desired, finely divided, so-called colloidal silica may also be present as a reinforcing agent in order to avoid settling phenonmena in the filler material, since this pure silicon oxide material, as is well known, is permeable to UV light, which is also more or less true for the visible region when it is sufficiently finely enough and uniformly dispersed in the resin mass. Furthermore, the masses may contain the customary fillers on the basis of $SiO_2$ or silicates.

As a result of the pigmenting filler to be used according to the invention, the dental filling material is sufficiently permeable for short wave light, which initiates the hardening or settling in conjunction with the photosensitizers and activators which may also be present, and which nevertheless possesses a sufficient absorption or reflection capacity for the rays of the visible region of the light spectrum, so that the above mentioned dark shining through does not occur in the case of their use, but the dental filling material has the usual dull white coloration of the teeth.

For the polymerization of the dental filler material according to the invention, the customary photo-initiators are used, such as, for instance, benzoin and its derivatives, benzil monoketals and 1,2-diketones. In order to achieve a quicker curing of these masses upon reaction to UV radiation and/or the short wave portion of the visible light (UVA radiation and near-UVA radiation), organic phosphites or tertiary amines may be additionally added.

In order to demonstrate the special effect of the addition of the white pigment according to the invention, comparative experiments were carried out. In this, so much white pigment was added in each case while using otherwise identical components of the tooth filler material, that the depth of polymerization (thickness of the layer) always amounted to 3.2±0.1 mm upon a 20 second exposure to a standard UV polymerization device (Uviolite).

This determination of the thickness of the layer was accomplished in such a way that a ring with an inside clearance of 5 mm and a thickness of 5 mm was charged with the mass that was to be polymerized; to cover the surfaces, thin glass plates were always used. For all experiments, the following standard mixture was used:

TABLE I

| Substance | Parts by weight |
| --- | --- |
| 2,2-bis-[p-(γ-hydroxy-propoxy-)phenyl]-propane-dimethacrylate | 100 |
| P-methoxy-phenol | 0.02 |
| benzil-dimethylketal | 0.5 |
| didecyl-phenyl-phosphite | 0.5 |
| microfine, pyrogenous silicic acid (silanized) | 5 |
| quartz (<60μ), pigmented acc. to tooth color (silanized) | 420 |

The polymerization is accomplished with the UV device in such a way that the quartz bar, at the end of which the UV rays emerge, was placed perpendicularly directly onto the upper glass plate. Subsequently, the thickness of the polymerized layer was measured. As a result of several tests, the quantity of the pertinent pigment was determined that results in the same value of polymerization depth of about 3.2 mm under otherwise equal conditions. The quantity of the respective white pigment added to this paste in each case is listed in column 2 of the following Table II. To measure the transparency, round, small plates with a diameter of 14.5 mm and a thickness of 0.6 mm were always used. To measure the light permeability, the Dr. Lange transparency measurement device was used by means of which the portion of the visible light passing through may be determined. In Table II, these data are given in percent in the last column.

TABLE II

| White Pigment | % of Paste | Visible Light Permeability |
|---|---|---|
| lithopone | 0.08 | 13.6% |
| titanium white R 25 (Kronos) | 0.05 | 17.9% |
| calcium fluoride (Merck) | 10 | 3.0% |
| zinc oxide G 6 | 0.017 | 29.1% |
| tin dioxide (Merck) | 0.32 | 9.2% |

The desired curing of the composition formulated according to the invention is achieved despite its partly more than 100 fold quantity of pigment. From the last column of Table II one can see that in the case of a polymerization depth of 3.2 mm, in the case of the use of the calcium fluoride material according to the invention, the permeability for visible light amounts to only about $\frac{1}{4}$–1/6 to that which results with the customarily used white pigments lithopone or titanium white. This fact is in agreement with the observation that in the case of the compositions prepared according to this invention, the above mentioned cosmetically undesirable dark shining through of the oral cavity is no longer observed even in the case of thin fillings.

EXAMPLE 1

A mixture is produced, containing

| Substance | Parts by Weight |
|---|---|
| 2,2-bis-[p-(γ-hydroxy-propoxy-)phenyl]-propane-dimethacrylate | 100 |
| p-methoxy-phenol | 0.02 |
| benzil-dimethylketal | 0.5 |
| didecyl-phenyl-phosphite | 0.5 |
| microfine, pyrogenous silicic acid (silanized) | 5 |

42 g of this mixture are then kneaded together with 189 g of tooth color pigmented quartz ($<60\mu$), which is silanized in the customary manner, as well as with 11 g of fine grained $CaF_2$ to form a tooth filler mixture.

Upon irradiation with the "Uviolite" UV polymerization device, one obtains polymers that show a pressure resistance or compressive strength of 3600 kp/cm². Dental fillings made from this composition are cosmetically outstanding; even in the case of continuous fillings in the frontal area of the teeth, they appear entirely tooth-like.

EXAMPLE 2

A mixture is produced, containing

| Substance | Parts by Weight |
|---|---|
| 2,2-bis-[p-(γ-hydroxy-propoxy-)phenyl]-propane-dimethacrylate | 100 |
| p-methoxy-phenol | 0.02 |
| α-methyl-benzoin-methyl ether | 0.5 |
| dioctyl phosphite | 0.8 |
| microfine, pyrogenous silicic acid (silanized) | 5 |

Proceeding as in example 1, one obtains a dental filling composition, the consistency of which is eminently suited for the production of fillings of teeth and for building up missing parts of teeth.

The fillings done with this are sufficiently opaque even in the frontal area of the teeth and cosmetically perfect.

EXAMPLE 3

A mixture is produced, containing

| Substance | Parts by Weight |
|---|---|
| Bis-hydroxymethyl-tricyclo [5.2.1.0$^{2,6}$]-decane-diacrylate | 100 |
| Jonol | 0.02 |
| p-methoxyphenol | 0.02 |
| phenanthrenequinone | 0.05 |
| N,N—dimethyl ethanolamine methacrylate | 4 |
| microfine, pyrogenous silicic acid (silanized) | 5 |

Next, a powder mixture is produced from 179.5 g silanized tooth color tinted quartz ($<60\mu$), and 9.1 g of fine grained calcium fluoride. 4 g of the liquid mixture is kneaded together with 18 g of the powder mixture and a dental filling composition which may be hardened with the short wave portion of the visible light is obtained.

Structures of missing parts of teeth produced with it and fillings in the front area of the tooth are opaque like teeth after curing and cosmetically perfect.

EXAMPLE 4

A liquid mixture is produced from

| Substance | Parts by Weight |
|---|---|
| bis-hydroxymethyl-tricyclo [5.2.1.0$^{2,6}$]-decane-diacrylate | 100 |
| p-methoxyphenol | 0.02 |
| Jonol | 0.02 |
| benzil dimethyl ketal | 0.6 |
| didecyl-phenyl-phosphite | 0.5 |
| microfine, pyrogenous silicic acid (silanized) | 15 |

Next, a powder mixture is produced from 153 g of silanized, tooth-color tinted barium glass ($<60\mu$; 25% by weight BaO) and 5 g of fine grained calcium fluoride.

g of the liquid mixture is kneaded together with 41 g of powder mixture.

Fillings and tooth constructions made from the resulting dental filler composition are opaque to X-rays and as a result of their opacity are also cosmetically excellently suited for the frontal area of the teeth.

EXAMPLE 5

A liquid mixture is produced from

| Substance | Parts by Weight |
| --- | --- |
| bis-hydroxymethyl-tricyclo [5.2.1.0$^{2,6}$]-decane-dimethacrylate | 100 |
| Jonol | 0.02 |
| p-methoxy phenol | 0.02 |
| benzil dimethyl ketal | 0.3 |
| didecyl-phenyl-phosphite | 0.5 |
| microfine, pyrogenous silicic acid (silanized) | 5 |

A heat polymer containing 40 parts by weight of poly-(bis-hydroxy-methyl-tricyclo[5.2.1.0$^{2,6}$]-decane-dimethacrylate) and 60 parts by weight of a microfine, pyrogenous silanized silicic acid is ground up, screened and tinted to tooth-like color.

11.2 g of this filler composition are mixed with 0.8 g of calcium fluoride and kneaded together with 5 g of the liquid mixture to form a dental filling composition.

This dental filling composition, after curing by irradiation, produces polishable tooth-like opaque fillings that are also cosmetically eminently suited in the frontal area of the teeth.

We claim:

1. In an opaque, photopolymerizable dental filling material comprised of acrylic acid ester compounds comprised of mono or polyfunctional acrylic or methacrylic ester compounds, a photoinitiator and a white pigment, the improvement wherein said material comprises from 1-20 percent by weight of finely divided calcium fluoride as said white pigment, based on the weight of the filling material.

2. The dental filling material of claim 1 wherein said calcium fluoride is present in an amount of 2-15 percent by weight.

3. The dental filling material of claim 1 or 2 wherein the calcium fluoride has a particle size of less than 60 microns.

4. The dental filling material of claim 3 wherein the calcium fluoride has a particle size of less than 10 microns.

5. The dental filling material of claim 1 further comprising silicon dioxide or silicate-based fillers.

6. The dental filling material of claim 1 wherein said photoinitiator is selected from the group consisting of benzoin and its derivatives, benzil monoketals and 1,2-diketones.

7. The dental filling material of claim 1 further comprising an activator selected from the group consisting of aliphatic or aromatic or mixed aliphatic-aromatic phosphites.

* * * * *

UNITED STATES PATENT AND TRADEMARK OFFICE
CERTIFICATE OF CORRECTION

PATENT NO. : 4,372,836
DATED : February 8, 1983
INVENTOR(S) : Werner Schmitt et al It is certified that error appears in the above—identified patent and that said Letters Patent is hereby corrected as shown below:

Column 4, line 60, that portion reading "g of the liquid mixture" should read --10 g of the liquid mixture--.

Signed and Sealed this

Twenty-fourth Day of May 1983

[SEAL]

Attest:

DONALD J. QUIGG

Attesting Officer

Acting Commissioner of Patents and Trademarks